(12) United States Patent
Clouatre et al.

(10) Patent No.: US 6,476,071 B1
(45) Date of Patent: Nov. 5, 2002

(54) CORRECTING POLYMORPHIC METABOLIC DYSFUNCTION WITH (−)-HYDROXYCITRIC ACID

(76) Inventors: Dallas L. Clouatre, 555 Bryant St. #357, Palo Alto, CA (US) 94301-1704; James M. Dunn, 3236 Hinsdale Pl., Littleton, CO (US) 80112

( * ) Notice: Subject to any disclaimer, the term of this patent is extended or adjusted under 35 U.S.C. 154(b) by 0 days.

(21) Appl. No.: 09/850,280

(22) Filed: May 7, 2001

(51) Int. Cl.$^7$ ............................................. A01N 37/00
(52) U.S. Cl. ....................... 514/557; 424/464; 424/422; 424/435; 514/866; 514/909
(58) Field of Search ................. 424/464, 422, 424/435; 514/866, 557, 909

(56) References Cited

U.S. PATENT DOCUMENTS

| | | | |
|---|---|---|---|
| 3,764,692 A | | 10/1973 | Lowenstein ................. 424/279 |
| 3,767,678 A | | 10/1973 | Guthrie et al. ........... 260/343.6 |
| 3,919,254 A | * | 11/1975 | Guthrie et al. ........... 260/343.6 |
| 3,993,668 A | * | 11/1976 | Guthrie et al. ........... 260/343.6 |
| 4,443,619 A | * | 4/1984 | Guthrie et al. ............... 549/518 |
| 5,626,849 A | * | 5/1997 | Hastings et al. .......... 424/195.1 |
| 5,656,314 A | * | 8/1997 | Moffett et al. .............. 426/271 |
| 5,783,603 A | * | 7/1998 | Majeed et al. ............... 514/574 |
| 5,911,992 A | * | 6/1999 | Braswell et al. ......... 424/195.1 |
| 5,914,326 A | * | 6/1999 | McCarty et al. ............ 514/188 |
| 6,207,714 B1 | * | 3/2001 | Clouatre et al. ............ 514/574 |
| 6,217,898 B1 | * | 4/2001 | Cavazza ...................... 424/450 |
| 6,221,901 B1 | * | 4/2001 | Shrivastava et al. ........ 514/458 |

OTHER PUBLICATIONS

Belfiore F, Iannello S. Insulin resistance in obesity: metabolic mechanisms and measurement methods. Mol Genet Metab. Oct. 1998;65(2):121–8.

Boden G, Chen X, Kolaczynski JW, Polansky M. Effects of prolonged hyperinsulinemia on serum leptin in normal human subjects. J Clin Invest. Sep. 1, 1997:100(5):1107–13.

Bowden C R, White KD, Tutwiler GF. Energy intake of cafeteria–diet and chow–fed rats in response to amphetamine, fenfluramine, (−) hydroxycitrate and haloxone. The Journal of Obesity and Weight Regulation 1985 Spring:4(1):5–13.

Ceddia RB, William WN Jr, Lima FB, Flandin P, Curi R, Giacobino JP. Leptin stimulates uncoupling protein–2 mRNA expression and Krebs cycle activity and inhibits lipidsynthesis in isolated rat white adipocytes. Eur J Biochem. Oct. 2000:267(19):5952–8.

Cohen B, Novick D, Rubinstein M. Modulation of insulin activities by leptin. Science. Nov. 15, 1996;274(5290):1185–8.

(List continued on next page.)

Primary Examiner—Thurman K. Page
Assistant Examiner—Lakshmi Channavajjala (57) ABSTRACT

A method whereby in an individual showing evidence of dysregulation of elements of the Polymorphic Metabolic Dysfunction (PMD), which is defined as the dysregulation of the metabolism of insulin, glucocorticoids, leptin, resistin and peroxisome proliferator-activated receptor γ (PPARγ), this regulation is improved when that person receives an appropriate administration of (−)-hydroxycitric acid. The potassium salt of (−)-hydroxycitric acid is a preferred form of the compound, followed by the sodium salt, then by the amide and other salt forms and derivatives of the acid. The regulation of Polymorphic Metabolic Dysfunction over any given period of time may be improved with a controlled release form of (−)-hydroxycitric acid. Controlled release can be used to provide a sustained and modulated amount of the active to the body as desired and therefore to regulate the use of the compound as Polymorphic Metabolic Dysfunction regulative agent.

30 Claims, 4 Drawing Sheets

OTHER PUBLICATIONS

Cooling J, Barth J, Blundell J. The high–fat phenotype: is leptin involved in the adaptive response to a high fat (high energy) diet? Int J Obes Relat Metab Disord. Nov. 1998, 22(11). 1132–5.

Fried SK, Ricci MR, Russell CD, Laferrere B. Regulation of leptin production in humans. J Nutr. Dec. 2000;130(12S Suppl):3127S–31S.

Fried SK, Lavau M, Pi–Sunyer FX. Role of fatty acid synthesis in the control of insulin stimulated glucose utilization by rat adipocytes J Lipid Res. Jul. 1981;22(5):753–62.

Fukuda H, Noguchi T, Iritani N. Transcriptional regulation of insulin receptor gene promoter in rat hepatocytes. Biochem Biophys Res Commun. Feb. 9, 2001, 280(5):1274–8.

Heymsfield SB, Allison DB, Vassell JR, Pietobelli A, Greenfield D, Nunez C. Garcinia cambogia (hydroxycitric acid) as a potential antiobesity agent: a randomized controlled trial. JAMA. 1998:280:1596–1600.

Ishihara K, Oyaizu S, Onuki K, Lim K, Fushiki T. Chronic(–)–hydroxycitrate administration spares carbohydrate utilization and promotes lipid oxidation during exercise in mice. J Nutr. Dec. 2000;130(12):2990–5.

Kee–Hong Kim, Kichoon Lee, Yang Soo Moon, and Hei Sook Sul. A Cysteine–rich Adipose Tissue–specific Secretory Factor Inhibits Adipocyte Differentiation. The Journal of BiologicalChemistry Apr. 6, 2001;276(14):11252–11256.

McCarty MF. Promotion of hepatic lipid oxidation and gluconeogenesisas a strategy for appetite control. Medical Hypotheses 1994;42:215–225.

Mattes RD, Bormann L, Effects of (–)–hydroxycitric acid on appetitive variables. Physiol Behav. Oct. 1, 2000;71(1–2):87–94.

Speigelman BM, Flier JS. Adipogenesis and obesity: rounding out the big picture. Cell. Nov. 1, 1996,87(3):377–89.

Steppan CM, Bailey ST, Bhat S, Brown EJ, Banerjee RR, Wright CM, Patel HR, Ahima RS Lazar MA. The hormone resistin links obesity to diabetes. Nature. Jan. 18, 2001;409(6818):307–12.

Sullivan, Ann C. and Joseph Triscari. Possible interrelationship between metabolite flux and appetite. In D. Novin, W. Wyriwicka and G. Bray, eds., Hunger: Basic Mechanisms and Clinical Implications (New York: Raven Press, 1976) 115–125.

Sullivan AC, Gruen RK Mechanisms of appetite modulation by drugs. Federation Proceedings 1985,44,1.139–144.

Sullivan AC, Triscari J. Metabolic regulation as a control for lipid disorders. I. Influence of (–)hydroxycitrate on experimentally induced obesity in the rodent. American Journal of Clinical Nutrition 1977;30:767.

Thampy GK, Haas MJ, Mooradian AD. Troglitazone stimulates acetyl–CoA carboxylase activity through a post–translational mechanism. Life Sci. Dec. 29, 2000,68(6):699–708.

Triscari J, Sullivan AC. Comparative effects of (–)–hydroxycitrate and (+)–allo–hydroxycitrate on acetyl CoA carboxylase and fatty acid and cholesterol synthesis in vivo. Lipids Apr. 1977,12(4):357–363.

Weinstein SP, Paquin T, Pritsker A, Haber RS. Glucocorticoid–induced insulin resistance: dexamethasone inhibits the activation of glucose transport in rat skeletal muscle by both insulin– and non–insulin–related stimuli, Diabetes, Apr. 1995;44(4):441–5.

Zakrzewska KE, Cusin I, Sainsbury A, Rohner–Jeanrenaud F, Jeanrenaud B. Glucocorticoids as counteregulatory hormones of leptin: toward an understanding of leptin resistance. Diabetes Apr. 1997;46(4):717–9.

Zakrzewska KE, Cusin I, Stricker–Krongrad A, Boss O, Ricquier D, Jeanrenaud B, Rohner Jeanrenaud F. Induction of obesity and hyperleptinemia by central glucocorticoid infusion in the rat. Diabetes Feb. 1999;48(2):365–70.

* cited by examiner

Figure 1
Daily Food Intake

CORRECTING POLYMORPHIC METABOLIC DYSFUNCTION WITH (−)-HYDROXYCITRIC ACID

RELATED PATENT APPLICATION BY THE SAME INVENTORS

Methods And Pharmaceutical Preparations For Normalizing Blood Pressure With (−)-Hydroxycitric Acid

BACKGROUND OF THE INVENTION

1. Field of the Invention

This invention relates to pharmaceutical compositions containing (−)-hydroxycitric acid useful for correcting Polymorphic Metabolic Dysfunction (PMD) in individuals in need thereof by influencing the metabolism of insulin, glucocorticoids and leptin and the relationship of these to the resistin-peroxisome proliferator-activated receptor γ (PPARγ) axis.

2. Description of Prior Art

According to the National Heart, Lung, and Blood Institute (1999), an estimated 97 million adults in the United States are overweight or obese, conditions which substantially raise their risks of morbidity from hypertension, dyslipidemia, type 2 diabetes, coronary heart disease, stroke, gallbladder disease, osteoarthritis, sleep apnea, respiratory problems, and endometrial, breast, prostate, and colon cancers. The percentage of overweight and obese men and women as a fraction of the populace at large has risen dramatically since 1960; in 1999, the estimated percentage of people in these categories has increased to approximately 55 percent of adults aged 20 years or older. The World Health Organization and the National Heart, Lung and Blood Institute of the National Institutes of Health have classified obesity as an epidemic inasmuch as the incidence of obesity in children and adults has increased by nearly 50% in the past decade. Significantly, it is increasingly recognized that unwanted weight often is indicative of intractable metabolic changes which are poorly treated over the long term with simple anorectic agents and which are substantially aggravated by bouts of dieting. As this suggests, the traditional focus upon weight loss and the treatment of obesity per se very commonly has been and remains nonproductive.

Leptin is the best known of the primary signals for the communication of body fat information to the central nervous system. Identification of this peptide in 1994 provided major new insights into the regulation of food intake, energy expenditure and body fat maintenance. It is now clear that this compound, which is derived primarily from fat cells, reduces food intake and increases the activity of the thermogenic components of the sympathetic nervous system in metabolically normal individuals.

Leptin production is stimulated by insulin and glucocorticoids, but inhibited by beta-adrenergic stimulation. Circulating levels of leptin are correlated with the level of body fat. The peptide exerts its effects through leptin receptors in the central nervous system. Modulation of neurons by leptin results in a reduction in the secretion of neuropeptide Y (NPY), a reduction in the secretion agouti-related protein (AGRP), and an increase in the secretion of proopiomelanocortin (POMC), the precursor of alpha-melanocyte-stimulating hormone (alpha-MSH), which reduces food intake. When researchers have examined the role of leptin in weight loss, injections in lean and obese subjects have had a dose-related effect upon weight and fat loss. However, there was significant discomfort at the injection site. For leptin to be clinically acceptable, the route of delivery must be improved. Alternatively, a solution would include indirect methods of influencing leptin secretion and/or sensitivity.

The use of a leptin-controlling alternative is all the more crucial because although injected leptin has shown some promise in reducing unwanted weight, its effects are not well understood and may be negative. A surprising and disappointing finding in one study was that some 30 percent of all the leptin-treated subjects actually gained weight during this trial, in comparison with one half of the placebo subjects. Moreover, inasmuch as leptin levels in the obese are already high—the obese may have three to five times as much leptin in their blood as do normal weight individuals, but only 20 percent more leptin in their brains—overcoming leptin resistance via exogenous leptin may require the continuous use of quite large amounts of the compound and bring its own array of side effects. As is the case of with insulin, which is taken by diabetics to overcome insulin resistance, excessive levels of leptin may not be innocuous. Indeed, studies have shown a strong correlation between elevated leptin levels and the insulin resistance syndrome. A causal model for leptin's role in insulin resistance has been offered by several teams of researchers. (Girard J. Is leptin the link between obesity and insulin resistance? Diabetes Metab. September 1997;23 Suppl 3:16–24; Spiegelman B M, Flier J S. Adipogenesis and obesity: rounding out the big picture. Cell. Nov. 1, 1996;87(3):377–89; Cohen B, Novick D, Rubinstein M. Modulation of insulin activities by leptin. Science. Nov. 15, 1996;274(5290): 1185–8.) Conversely, it might be argued that the initial issue is that of insulin resistance itself and that this metabolic syndrome or Syndrome X blunts the normal physiologic effects of leptin. (Boden G, Chen X, Kolaczynski J W, Polansky M. Effects of prolonged hyperinsulinemia on serum leptin in normal human subjects. J Clin Invest. Sep. 1, 1997;100(5):1107–13.)

Adrenal glucocorticoids, such as cortisol and corticosterone, play an important role in the neuroendocrine control of food intake and energy expenditure. Experimental evidence demonstrates that glucocorticoids are critical for the development and maintenance of obesity, that is, obesity is linked to increases in glucocorticoid production and/or to hyperresponsiveness to glucocorticoids in the hypothalanic-pituitary-adrenal axis. Glucocorticoids have been shown to be necessary if the chronic intracerebroventricular infusion of neuropeptide Y is to produce obesity and related abnormalities. Obversely, adrenalectomy in animals with a lesion to the ventromedial hypothalamus will reverse obesity. In humans, excess production of glucocorticoids produces modest obesity, and destruction of the adrenal glands is associated with a loss of body fat. Significantly, it has been found that glucocorticoids inhibit the body weight-lowering effect of leptin. (Zakrzewska KE, Cusin I, Sainsbury A, Rohner-Jeanrenaud F, Jeanrenaud B. Glucocorticoids as counterregulatory hormones of leptin: toward an understanding of leptin resistance. Diabetes April 1997;46(4):7 17–9.)

Both neuropeptide Y and leptin act within the hypothalamus, yet the effects of the glucocorticoids in promoting weight gain may be realized peripherally as well as centrally. In an animal experiment, a continuous central glucocorticoid infusion for 3 days resulted in marked sustained increases in food intake and body weight relative to saline-infused controls. The infusion, which was sufficient to abolish endogenous corticosterone output, produced hyperinsulinemia, hypertriglyceridemia, and hyperleptinemia, three salient abnormalities typical of obesity syndromes. Central glucocorticoid infusion also produced a marked decrease in the expression of uncoupling protein (UCP)-1 and UCP-3 in brown adipose tissue and a decrease in the expression of UCP-3 in muscle, i.e., infusion resulted in a marked decrease in the expression of the "thermogenic" proteins. Chronic central glucocorticoid administration increased hypothalamic levels of neuropeptide Y. (Zakrzewska K E, Cusin I, Stricker-Krongrad A, Boss 0, Ricquier D, Jeanrenaud B, Rohner-Jeanrenaud F. Induction of obesity and hyperleptinemia by central glucocorticoid infusion in the rat. Diabetes February 1999;48(2):365–70.) Through perhaps unrelated means, glucocorticoids induce insulin resistance. (Weinstein SP, Paquin T, Pritsker A, Haber R S. Glucocorticoid-induced insulin resistance: dexamethasone inhibits the activation of glucose transport in rat skeletal muscle by both insulin- and non-insulin-related stimuli. Diabetes. April 1995;44(4):441–5.)

Closely related to the physiologic actions of insulin and leptin are the linked actions of resistin and peroxisome proliferator-activated receptor γ (PPARγ). Only very recently, a team of researchers demonstrated that adipocytes secrete a unique signaling molecule which they named resistin (for resistance to insulin). Circulating resistin levels are decreased by the anti-diabetic drug rosiglitazone and other thiazolidinedione (TZD) drugs, but increased in diet-induced and genetic forms of obesity. Administration of an anti-resistin antibody improves blood sugar and insulin action in mice with diet-induced obesity. Conversely, treatment of normal mice with recombinant resistin impairs glucose tolerance and insulin action. Insulin-stimulated glucose uptake by adipocytes is enhanced by neutralization of resistin and is reduced by resistin treatment. Resistin is thus a hormone that potentially links obesity to diabetes. There is a very notable overlap in the physiologic functions controlled by resistin and those controlled by PPARγ. Moreover, as is shown by the efficacy of the TZD drugs, which target PPARγ and also reduce resistin levels, the cellular regulatory mechanisms governing resistin and PPARγ appear to be linked. (Steppan C M, Bailey S T, Bhat S, Brown E J, Banerjee R R, Wright C M, Patel H R, Ahima R S, Lazar M A. The hormone resistin links obesity to diabetes. Nature. Jan. 18, 2001;409(6818):307–12; Kee-Hong Kim, Kichoon Lee, Yang Soo Moon, and Hei Sook Sul. A Cysteine-rich Adipose Tissue-specific Secretory Factor Inhibits Adipocyte Differentiation. The Journal of Biological Chemistry Apr. 6, 2001;276(14):11252–11256.) From another angle, new research is increasingly showing that the transcription of the insulin receptor gene promoter is controlled by the same regulatory sequences which govern leptin, fatty acid synthase and other glucose/insulin responsive cellular elements. (Fukuda H, Noguchi T, Iritani N. Transcriptional regulation of insulin receptor gene promoter in rat hepatocytes. Biochem Biophys Res Commun. Feb. 9, 2001;280(5):1274–8.)

Unclear in this picture is whether the core syndrome is insulin resistance, sometimes termed Syndrome X or the "metabolic" syndrome, or whether at work are overlapping and causally-related mechanisms. In recognition of the fact that (1) elevated insulin levels can lead to elevated leptin levels, which in turn will promote insulin resistance; (2) elevated leptin levels and subsequent leptin resistance may prove in some cases to be the initial alteration which induces insulin resistance; (3) sustained elevations in the glucocorticoids may promote either or both insulin and/or leptin resistance through the mechanisms outlined and yet others; and (4) resistin and/or the resistin-PPARγ axis, similarly, is tied to insulin resistance, leptin levels, etc., the authors propose to view excessive weight gain as often being indicative of a Polymorphic Metabolic Dysfunction (PMD) in which these factors are linked.

Unrelated to these recent developments in obesity research according to published literature are the actions of (−)-hydroxycitric acid. (−)-Hydroxycitric acid (abbreviated herein as HCA), a naturally-ocurring substance found chiefly in fruits of the species of Garcinia, and several synthetic derivatives of citric acid have been investigated extensively in regard to their ability to inhibit the production of fatty acids from carbohydrates, to suppress appetite, and to inhibit weight gain. (Sullivan AC, Triscari J. Metabolic regulation as a control for lipid disorders. I. Influence of (−)-hydroxycitrrate on experimentally induced obesity in the rodent. American Journal of Clinical Nutrition 1977;30:767.)

Weight loss benefits were first ascribed to HCA, its salts and its lactone in U.S. Pat. No. 3,764,692 granted to John M. Lowenstein in 1973. The claimed mechanisms of action for HCA, most of which were originally put forth by researchers at the pharmaceutical firm of Hoffimann-La Roche, have been summarized in at least two United States Patents. In U.S. Pat. No. 5,626,849 these mechanisms are given as follows: "(−) HCA reduces the conversion of carbohydrate calories into fats. It does this by inhibiting the actions of ATP-citrate lyase, the enzyme which converts citrate into fatty acids and cholesterol in the primary pathway of fat synthesis in the body. The actions of (−) HCA increase the production and storage of glycogen (which is found in the liver, small intestine and muscles of mammals) while reducing both appetite and weight gain. (−) Hydroxycitric acid also causes calories to be burned in an energy cycle similar to thermogenesis . . . (−) HCA also increases the clearance of LDL cholesterol . . . . " U.S. Pat. No. 5,783,603 further argues that HCA serves to disinhibit the metabolic breakdown and oxidation of stored fat for fuel via its effects upon the compound malonyl CoA and that gluconeogenesis takes place as a result of this action. The position that HCA acts to unleash fatty acid oxidation by negating the effects of malonyl CoA with gluconeogenesis as a consequence (McCarty MF. Promotion of hepatic lipid oxidation and gluconeogenesis as a strategy for appetite control. Medical Hypotheses 1994;42:215–225) is maintained in U.S. Pat. No. 5,914,326.

HCA has not been suggested in any published literature as a compound with the ability to lower blood sugar levels, to improve glucose metabolism, to lower insulin levels, to influence glucocorticoid levels, to alter leptin levels or to have any influence upon resistin or PPARγ. Indeed, the precise mechanisms of action of the drug remain largely unexplained. For instance, the original pharmaceutical research on HCA performed at Hoffman-La Roche failed to find significant changes in either blood glucose levels or blood insulin levels, undoubtedly in large part due to the fact that almost all of that research used diets which consisted preponderantly of glucose as the source of calories (e.g., 70% glucose diets were typically employed to encourage lipogenesis). Such a diet might easily mask the effects of a compound which amplified the body's normal physiologic mechanisms of glucose control rather than substituting for these or even blocking normal pathways. The conclusion of the Roche researchers was that "no significant differences in plasma levels of glucose, insulin, or free fatty acids were detected in (−)-hydroxycitrate-treated rats relative to controls. These data suggest that peripheral metabolism, defined in the present context as metabolite flux, may be involved in appetite regulation . . . " (Sullivan, Ann C. and Joseph Triscari. Possible interrelationhip between metabolite flux and appetite. In D. Novin, W. Wyriwicka and G. Bray, eds., Hunger: Basic Mechanisms and Clinical Implications (New York: Raven Press,1976) 115–125.) No Roche data was ever published linking HCA to changes in glucocorticoid levels; leptin, resistin and PPARγ had not even been discovered at the time of the Roche HCA trials.

Some early preliminary work showed that labeled $^{14}C$ attached to HCA found its way into the brain. (Sullivan A C, Triscari J. Metabolic regulation as a control for lipid disorders. I. Influence of (−)-hydroxycitrate on experimentally induced obesity in the rodent. American Journal of Clinical Nutrition 1977;30:767.) However, work published by the same authors at a later date indicated otherwise. "Hydroxycitrate, chlorocitrate, and epoxyaconitate, compounds that are structurally similar to the tricarboxylic acid cycle intermediate citric acid, but that differ markedly in biochemical activity, have recently been evaluated in animals for effects on appetite. Because neither these compounds nor their metabolites enter the brain, their primary effects on food intake occur by peripheral mechanisms." (Sullivan A C, Gruen R K. Mechanisms of appetite modulation by drugs. Federation Proceedings 1985;44, 1:139–144.)

Despite the published conclusions by the Roche researchers, the present inventors have discovered that HCA, in fact, does reduce glucocorticoid, insulin and leptin levels in animals which are fed a diet in which the calories are not derived predominantly from simple sugars. The inventors, moreover, have found that these reductions act independently of HCA's established appetite-suppressing effect to lead to a lasting reduction in the tendency to gain weight even when food intake increases to the level of that eaten by controls. Whether this benefit is a result of a disinhibited expression of uncoupling proteins (UCP-1 and UCP-3, primarily) or is a result of a less direct effect upon leptin, PPARγ and/or insulin sensitivity has not been conclusively established. The present authors consider the effect as arising from the correction of one or more arms of the Polymorphic Metabolic Syndrome (PMD) described above.

Of the readily available forms of HCA, only the potassium and sodium salts of HCA are absorbed well enough to be effective agents at tolerable levels of ingestion. Reasons for this are given in the inventors' copending U.S. Patent Application "Potassium (−)-Hydroxycitric Acid Methods For Pharmaceutical Preparations For Stable And Controlled Delivery." Derivatives of HCA may also be active and effective in this regard. (U.S. Pat. Nos. 3,993,668; 3,919, 254; 3,767,678.) Liquid forms of HCA currently in use are irritating to the digestive system, depending upon the dose, and may cause an elevation of stress hormones as a result. Researchers have found that animals given high doses of the liquid form of the compound orally exhibit stress behavior. (Ishihara K, Oyaizu S, Onuki K, Lim K, Fushiki T. Chronic (−)-hydroxycitrate administration spares carbohydrate utilization and promotes lipid oxidation during exercise in mice. J Nutr. December 2000;130(12):2990–5.) Similarly, the ethylenediamine salts of HCA used in some of the later research performed by Hoffman-La Roche are known to be irritating and even toxic, properties which are due to the ethylenediamine ligand and not to the HCA. In contrast to the quite limited efficacy found with the calcium salt and some other delivery forms of HCA, the impact of ingestion of appropriate amounts of the appropriate salts of HCA upon corticosterone levels has been positive, as has the impact upon insulin and leptin levels in diets which calorically are not predominantly composed of sugars.

This picture is complicated considerably by the fact that all of the more recent and more thorough clinical trials on HCA not only have failed to produce appetite suppression, but also—and surprisingly in light of the claims made in several HCA patents already granted—have produced trends toward weight gain. (Heymsfield S B, Allison D B, Vasselli J R, Pietrobelli A, Greenfield D, Nunez C. Garcinia cambogia (hydroxycitric acid) as a potential antiobesity agent: a randomized controlled trial. JAMA. 1998;280:1596–1600; also Mattes R D, Bormann L. Effects of(−)-hydroxycitric acid on appetitive variables. Physiol Behav. Oct. 1, 2000;71 (1–2):87–94.) Although they did not pursue the matter thoroughly, two Roche researchers in 1977 showed that HCA in the cytosol of the cell will activate acetyl CoA carboxylase similarly to the citrate it resembles. The effect of this property is that in diets which supply a source of acetyl CoA to the cytosol other than via citrate derived from the mitochondria, which means diets containing appreciable amounts of fat or alcohol as opposed to diets consisting almost exclusively of carbohydrates, HCA may increase the synthesis of fats and weight gain. (Triscari J, Sullivan A C. Comparative effects of (−)-hydroxycitrate and (+)-allohydroxycitrate on acetyl CoA carboxylase and fatty acid and cholesterol synthesis in vivo. Lipids April 1977;12(4): 357–363.)

Not a single one of the patents which have been granted to date for the employment of HCA as an antiobesity agent (U.S. Pat. Nos. 3,764,692; 5,626,849; 5,783,603; 5,914,326 and others proposing the use of HCA as an adjunctive ingredient) has indicated any awareness of this paradoxical effect, an effect which has led to either null or negative results in the major clinical trials with HCA up to the point of this writing. Two very recently granted HCA patents are no more enlightening on the paradoxical qualities of HCA. In U.S. Pat. No. 6,217,898 which tested calcium hydroxycitrate either alone or in combination with L-carnitine, the diet used consisted of 50% glucose and only 1% calories from fat in animals given calcium hydroxycitrate (CaHCA) as 1–2% of their total food intake. The human equivalent would be at least 10–20 grams intake of CaHCA per day on a diet which is pharmaceutically fat free. In fact, CaHCA is very poorly absorbed, and the published research literature found in peer-reviewed journals as already discussed would seem to indicate that the test results given in U.S. Pat. No. 6,217,898 will not be reproducible outside of the narrow diet employed. No mention is made in this patent of the variables given above as aspects of PMD, i.e., insulin, leptin, glucocorticoids, resistin or PPARγ.

Similarly, U.S. Pat. No. 6,221,901 teaches a method for the production of magnesium (−)-hydroxycitrate and makes claims for the benefits of magnesium when (−)-hydroxycitric acid is employed as the ligand in conjunction with at least one indicated vitamin or additional metal. The experimental dosages used to generate the animal data were extraordinarily high (500 mg MgHCA/kg body weight/day in the rats and 750 mg/kg body weight/day in rabbits). In the in vivo animal experiments, there were no separate non-HCA magnesium arms and therefore no proof that any other good source of magnesium would not have yielded statistically similar results. Further, the authors of U.S. Pat. No. 6,221,901 give no evidence that the very low dosage of MgHCA listed in the claims—starting at 50 mg MgHCA per day—will provide any benefits to humans inasmuch as even the individual rats in the tests cited were being dosed at roughly 125 mg MgHCA/day, i.e. rats weighing roughly 0.3 kg were tested with a total daily dose of MgHCA more than twice that claimed to be efficacious in a 70 kg human. Likewise, the 3 kg rabbits received approximately 250 mg MgHCA each day, yet the test results are extrapolated to a 70 kg human ingesting only 50 mg MgHCA per day. No mention is made in the patent of aspects of PMD, i.e., no mention is made of issues involving the metabolism of insulin, leptin, glucocorticoids, resistin or PPARγ.

Animal trials conducted by the present inventors have confirmed the danger of the weight gain effect of HCA when the compound is delivered at an inadequate dosage level or in an inappropriate manner of intake, especially in conjunction with a diet containing nontrivial amounts of fats. Certainly, the typical American dietary pattern in which calories derived from fats account for at least 30% of the total caloric intake is sufficient to cause supplementation with HCA to upregulate acetyl CoA carboxylase and, subsequently, the synthesis of fatty acids from acetyl CoA.

In discovering the ability of HCA to correct Polymorphic Metabolic Dysfimction, the present authors have uncovered that HCA exhibits a twofold biphasic nature. First, the weight loss effects found with HCA during the first several weeks of use appear to be dependent primarily upon anorexia caused by a delay in gastric emptying. The suggestion by Roche researchers that the appetite suppression found with the compound is dependent upon glucoreceptors in the liver has never been fully reconciled with the rapid onset of satiety caused by HCA once a meal was begun as long as the compound was already in the system. However, action upon receptors in the small intestine and delay in gastric emptying does explain the observed effects of the compound quite handily. Moreover, although Roche never published data on HCA and gastric emptying in journal articles or in other scientific forums, the company did obliquely reveal that HCA works by delaying stomach emptying in its patents on chlorocitric acids (e.g., U.S. Pat. No. 4,443,619.) Moreover, various documents detailing Roche animal experiments found in the public domain show that the appetite-controlling aspects of HCA decline after several weeks of ingestion of the compound, and the present authors can support this with their own animal findings, which indicate a steep drop-off in anorectic effect which becomes significant sometime after about six weeks of use. The effects of HCA upon Polymorphic Metabolic Dysfunction remain, however, after the effects upon appetite have disappeared.

Second, HCA is biphasic in at least one other sense, and that is in its differential outcome depending upon whether it is supplied at an adequate level and/or in an appropriate manner of delivery. The present authors' animal experiments have confirmed that some HCA salts sold commercially and utilized for failed clinical trials will cause weight gain in animals under experimental conditions in which fats account for 30% of ingested calories. These commercial salts appear to suffer from poor assimilation and/or there is some problem with the nature of the compound which is delivered into the body inasmuch as even the so-called solubilized salts which are mixtures of potassium and calcium fail to reduce weight gain in animal experiments. In contradistinction to these commercial HCA products, the same amount of HCA delivered from a fairly good quality potassium salt under the same conditions as indicated above and discussed below under Preferred Embodiments inhibited weight gain in this animal experiment. Furthermore, in at least one animal experiment, the use of a patented admixture (as described in U.S. Pat. No. 5,626,849 and produced according to the examples given there) which employed a poor quality HCA salt yielded weight loss benefits which were not better than those found with the salt alone or with placebo. Hence, under most circumstances, the quality of the source of HCA is likely to be more significant than will be any auxiliary compounds claimed to augment the efficacy of the HCA.

No prior art suggests that HCA can be used to counteract elevated glucocorticoid levels, hyperinsulinemia or hyperliptinemia, nor that HCA can affect resistin or peroxisome proliferator-activated receptor γ. No prior art teaches that HCA can counteract unwanted effects of elevated levels of these hormones and thus normalize metabolic functions. The present inventors therefore have discovered a novel means of correcting the Polymorphic Metabolic Dysfunction.

SUMMARY OF THE INVENTION

The inventors have discovered that HCA is useful in reducing or even correcting Polymorphic Metabolic Dysfunction (PMD), here defined as a syndrome in which there resistance to the actions of insulin and/or leptin, usually both, with a pathological involvement of the glucocorticoids and dysregulation of resistin and/or peroxisome proliferator-activated receptor γ (PPARγ). This action by HCA with regard to PMD has not heretofore been recognized. The benefits of HCA in reducing polymorphic metabolic dysfunction are especially pronounced with the use of the preferred salt of the acid, potassium hydroxycitrate, and may be further potentiated by the use of a controlled-release form of the compound. The discovery that HCA has Polymorphic Metabolic Dysfunction-moderating effects allows for the creation of novel and more efficacious approaches to preventing obesity, for maintaining normal metabolic functioning even in the face of diet and exercise habits which are less than ideal, for preventing the development of insulin resistance and its attendant well-documented health risks, and for preventing or moderating the damaging effects which are associated with elevated levels of circulating insulin, leptin, glucocorticosteroids, resistin and/or dysfunctions involving peroxisome proliferator-activated receptor γ. Furthermore, this discovery makes possible the development of adjuvant modalities which can be used to improve the results realized, for instance, from treatment with leptin and other "weight loss" compounds while at the same time reducing the side effects normally found with such drugs. HCA delivered in the form of its potassium salt is efficacious at a daily dosage (bid or tid) of between 750 mg and 10 grams, preferably at a dosage of between 3 and 6 grams for most individuals. A daily dosage above 10 grams might prove desirable under some circumstances, such as with grossly obese or resistant individuals, but this level of intake is not deemed necessary under normal conditions.

OBJECTS AND ADVANTAGES

It is an objective of the present invention to provide a method for treating or ameliorating Polymorphic Metabolic Dysfunction. It is a further object of the present invention to provide a means of treating or ameliorating Polymorphic Metabolic Dysfunction by addressing the primary elements of this disorder: elevated insulin, leptin and stress hormone levels as well as dysregulation of resistin and/or peroxisome proliferator-activated receptor γ. These elevations and dysfunctions are usually accompanied by resistance to the actions of insulin and leptin. It is yet a further advantage of the present invention to provide a means—one which is accompanied by few or no side effects—of maintaining proper metabolic functioning and energy expenditure as well as stabilizing weight without resort to caloric restriction or special diets. Knowledge of the present invention has the advantage of allowing the use of forms of (−)-hydroxycitric acid, including especially through controlled release formulations, as adjuvants to obesity drugs and to drugs designed to stabilize or improve long term energy balance. These objects and advantages are not derived from the anorectic actions commonly claimed for the use of HCA as an anti-obesity agent—actions which animal trials indicate may not last longer than roughly six or seven weeks, in any event—but rather are found with the extended use of the compound and rely upon mechanisms not heretofore uncovered.

DESCRIPTION OF THE PREFERRED EMBODIMENTS

The free acid form and various salts of (−)-hydroxycitric acid (calcium, magnesium, potassium, sodium and mixtures of these) have been available commercially for several years. Any of these materials can be used to fulfill the invention revealed here, but with varying degrees of success. For reasons given in our co-pending U.S. Pat. Application "Potassium (−)-Hydroxycitric Acid Methods For Pharmaceutical Preparations For Stable And Controlled Delivery," these materials are generally useful in this descending order of efficacy: potassium salt, sodium salt, free acid, magnesium salt, calcium salt. A novel method for improving the efficacy and workability of these forms is provided in that application. Exact dosing will depend upon the form of HCA used, the weight of the individual involved, and the other components of the diet. In part due to the need to control the release of this hypoglycemic agent in diabetics, as outlined in the inventors' recently accepted U.S. Pat. No. 6,207,714 covering the employment of HCA as hypoglycemic agent, a controlled release preparation is to be preferred. Controlled release can also be expected to improve results by aiding in maintaining a sustained exposure to the drug as required for therapy.

The previously patented hydroxycitric acid derivatives (mostly amides and esters of hydroxycititric acid, the patents for which are now expired, to wit, U.S. Pat. Nos. 3,993,668; 3,919,254; and 3,767,678) likely are roughly equivalent to the HCA sodium salt in efficacy and can be applied as hypotensive agents at taught herein by one skilled in the art. However, for the purposes of reducing stress hormone (glucocorticoid) levels, hydroxycitric acid in its free acid form and in its lactone form may prove to be the least desirable of currently available forms of the compound. These forms are irritating to the gastrointestinal tract and thus, in higher dosages, may lead to elevations in stress response. Similarly, hydroxycitric acid in its free acid form and in its lactone form are less desirable for long term use due to their ability to chelate minerals and thereby perhaps lead to mineral loss.

EXAMPLE 1

Effects Upon Gastric Emptying

Evidence that HCA during the initial weeks of usage likely reduces appetite through an effect upon gastric emptying emerged from a clinical trial. Previously, Roche, in public documents, had shown that HCA can control food intake if administered in one large bolus dose or in two much smaller dosages given prior to meals. This indicates a clearance rate of the drug. HCA given after a meal has already begun has no impact upon food intake. However, HCA given continuously in the food supply to rats, animals which eat more or less continuously during waking hours if food is available, will, again, reduce food intake. Roche argued in public documents that the appetite suppressing actions of HCA depend upon the activation of glucoreceptors in the liver, yet this particular explanation for a peripherally-acting agent (no effect upon the central nervous system) seems inadequate in light of the very quick onset of satiety after a meal has begun in experiments in which animals are restricted to two meals per day after gavage with the compound. It also seems to be inadequate given that in an experiment in which the rats' satiety center of the brain had been destroyed there still was appetite suppression. Hepatic glucoreceptor activation of the vagus nerve probably would have no impact upon the satiety center of the brain under such circumstances. Hence, meals clearly trigger some mechanism which has been activated by HCA, yet it is unlikely that sufficient calories from a meal can reach the liver in time to account for the rapid onset of satiety or satisfy these other conditions just mentioned. In a drug which acts at least in part upon receptors in the small intestine, these factors, however, would no longer be problematic.

Data on human usage emerged from a multi-week pilot open clinical weight loss trial with extremely obese patients which was undertaken to gauge the effects of a pouch delivery form of a potassium salt of (−)-hydroxycitrate under the normal circumstances faced in clinical practice with this patient population. Sixteen patients were enrolled, three of whom were diabetics on medications and several others who were suspected of suffering from insulin resistance. The patients ingested 3–4 grams of HCA per day in two divided doses. Aside from being informed that they must eat a carbohydrate-containing meal within one hour of taking the HCA and that they should avoid eating late in the day, they were not instructed to follow any special diet or exercise plan outside their normal habits and no caloric restriction was imposed. This particular form of potassium (−)-hydroxycitrate delivery typically was mixed into water or juice and consumed at mid-morning and mid-afternoon. The delivery was a water-soluble immediate release form. It was a pre-commercial preparation and nearly all of the patients complained regarding the inconvenience and poor taste of the product, albeit there were no other issues of tolerability.

A number of patients continued on the program for 6 weeks. However, most patient data was good for only 3 weeks because two of the diagnosed diabetics experienced severe hypoglycemic reactions. Several other patients experienced good appetite suppression, yet also complained of episodic tiredness at the beginning of the program, a sign of low blood sugar. Two patients subsequently were placed on phentermine. One patient who followed the program for 10 weeks with excellent weight loss (32 pounds over 10 weeks) found that his tendency toward elevated blood sugar was stabilized during the program. This patient returned to his prior experiences of infiequent hypoglycemia roughly one week after he had left the program, something which suggests a carryover effect from the compound. The average weight loss over the 3 week period for these 14 patients was approximately 3.1 pounds per person per week. In the eight patients with hypertension, the compound showed a surprising ability to normalize blood pressure. The clinical decision was made that potassium (−)-hydroxycitrate in an immediate release format can exercise a strong hypoglycemic effect in diabetics and that it appears to influence blood sugar levels in protodiabetics, as well. At therapeutically effective dosages, HCA probably should be used with diabetic populations only under a physician's care.

When questioned regarding degree of appetite suppression and compliance patterns in taking the HCA, many patients noted that not only did the compound make them "feel fuller faster," but also that they seemed to feel full for a longer period of time. The authors speculated that rapidity of onset of satiety may involve intestinal glucoreceptors and that continued satiety could involve these same receptors or some allied mechanism. For instance, protease inhibitors which block trypsin and chymotrypsin may enhance satiety by preventing digestion of the cholecystokinin-releasing peptide (CCK-RP), a peptide which is secreted into the gut lumen during meals. CCK-RP can then stimulate release of the satiety peptide CCK from endocrine cells in the small intestine.

The intuition of the present authors has been upheld by experimental data. Hoffman-La Roche in the form of the inventors Guthrie, et al. in a patent filing covering the use of chlorocitric acids (U.S. Pat. No. 4,443,619) teach in their Example 25 that the trisodium salt of (−)-hydroxycitric acid under experimental conditions more than doubled the contents of the stomach of rats after a three hour meal in comparison with the stomach contents found in the controls (1973±154 versus 884±145 dpm×$10^3$, which is 223% of control). The clear implication is that the correction of the polymorphic metabolic syndrome is an effect unrelated to the appetite suppression for which HCA is normally touted.

EXAMPLE 2

The Biphasic Qualities of (−)-Hydroxycitric Acid

The published literature on HCA recognizes both the temporal and the dosage biphasic effects mentioned above, albeit very little is made of these. However, no patent granted on the use of HCA to date, insofar as the present authors are aware, makes mention of either effect. Indeed, the weight loss or anti-obesity claims of prior HCA patents would seem to rest largely or even entirely upon the observed appetite-suppressing effects of HCA, and these effects seem to disappear within seven weeks. (Sullivan A C, Triscari J. Metabolic regulation as a control for lipid disorders. I. Influence of (−)-hydroxycitrrate on experimentally induced obesity in the rodent. American Journal of Clinical Nutrition 1977;30:767.) No previous patent on HCA mentions the problematic use of the compound in conjunction with diets which contain significant amounts of fat. Hence the dosage levels commonly suggested, such as in the patent of Hastings, et al. (U.S. Pat. No. 5,626,849), which patent never tested its claims in either animals or humans, will lead to elevated rates of production of fats and to either null results or even weight gain under most most human dietary practices in which fats contribute at least 30% of calories. Recent negative clinical results using the amounts of HCA commonly suggested, including in the issued U.S. patents, bear out the truth of this observation. These trials used 1.5 grams and 1.2 grams of HCA per day derived from calcium (−)hydroxycitrate and ingested in divided doses before meals. (Heymsfield S B, Allison D B, Vasselli J R, Pietrobelli A, Greenfield D, Nunez C. Garcinia cambogia (hydroxycitric acid) as a potential antiobesity agent: a randomized controlled trial. JAMA. 1998;280:1596–1600; also Mattes RD, Bormann L. Effects of (−)-hydroxycitric acid on appetitive variables. Physiol Behav. Oct. 1, 2000;71(1–2):87–94.)

Figure 1:
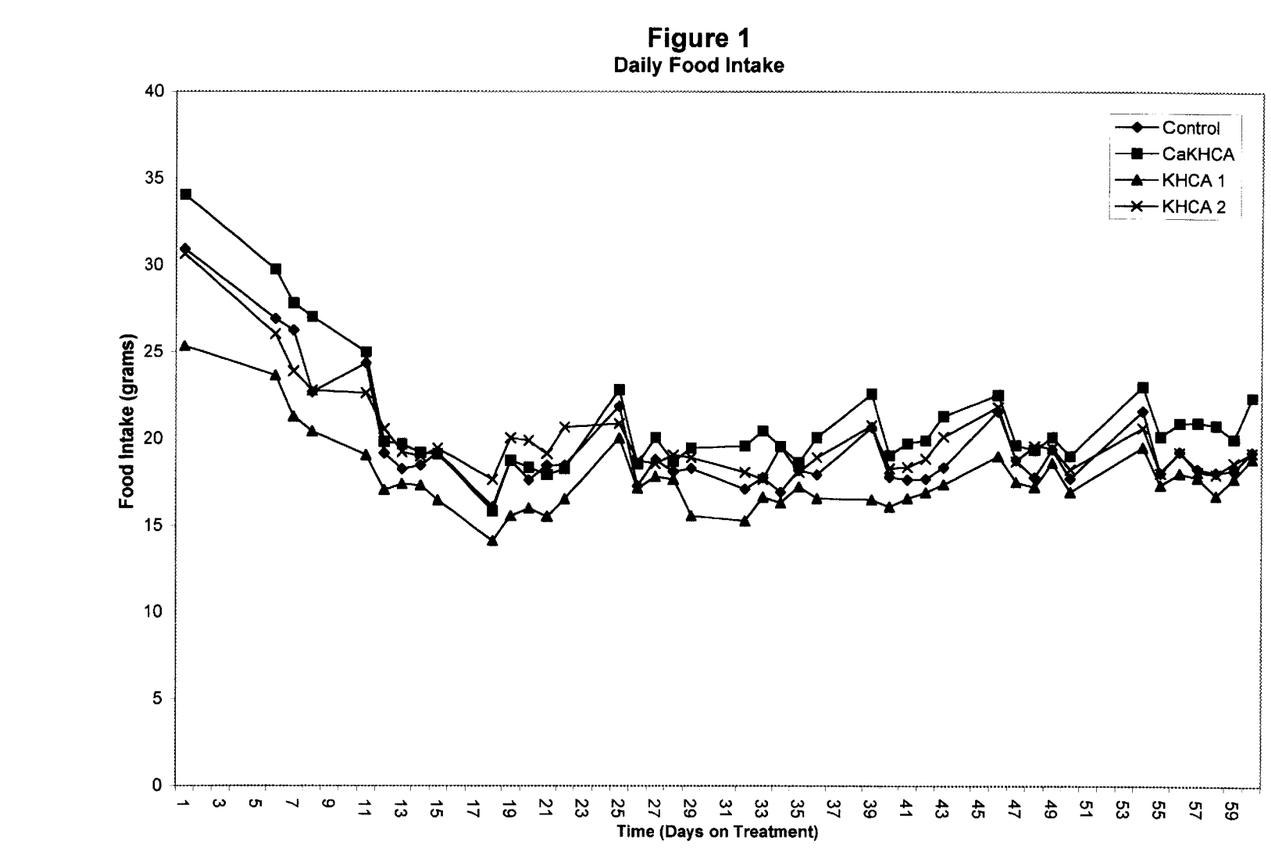
FIGS. 1 and 4 show the effect of HCA on the food intake as a daily change and cumulative intake, respectively.
Figure 2:
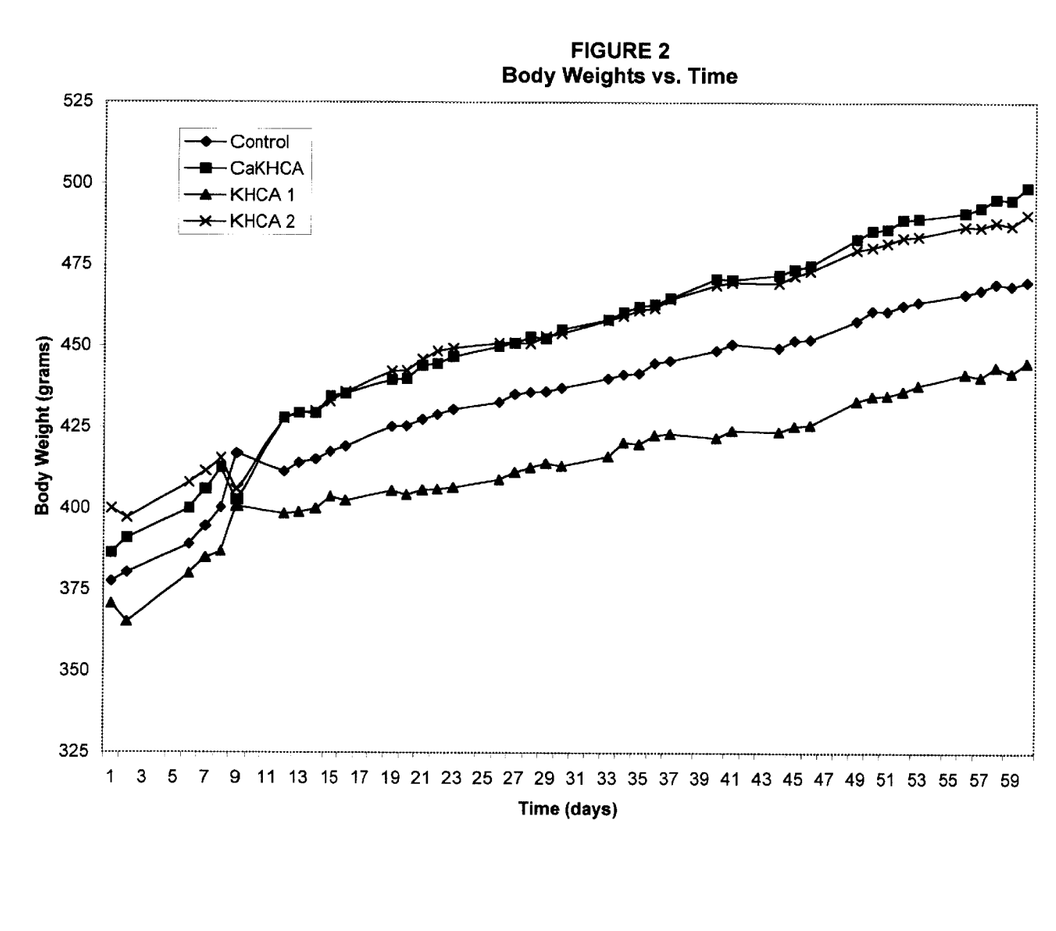
FIGS. 2 and 3 show the effect of HCA in total body weight and the change in body weigh in relationship to starting weight, respectively.
Figure 3:
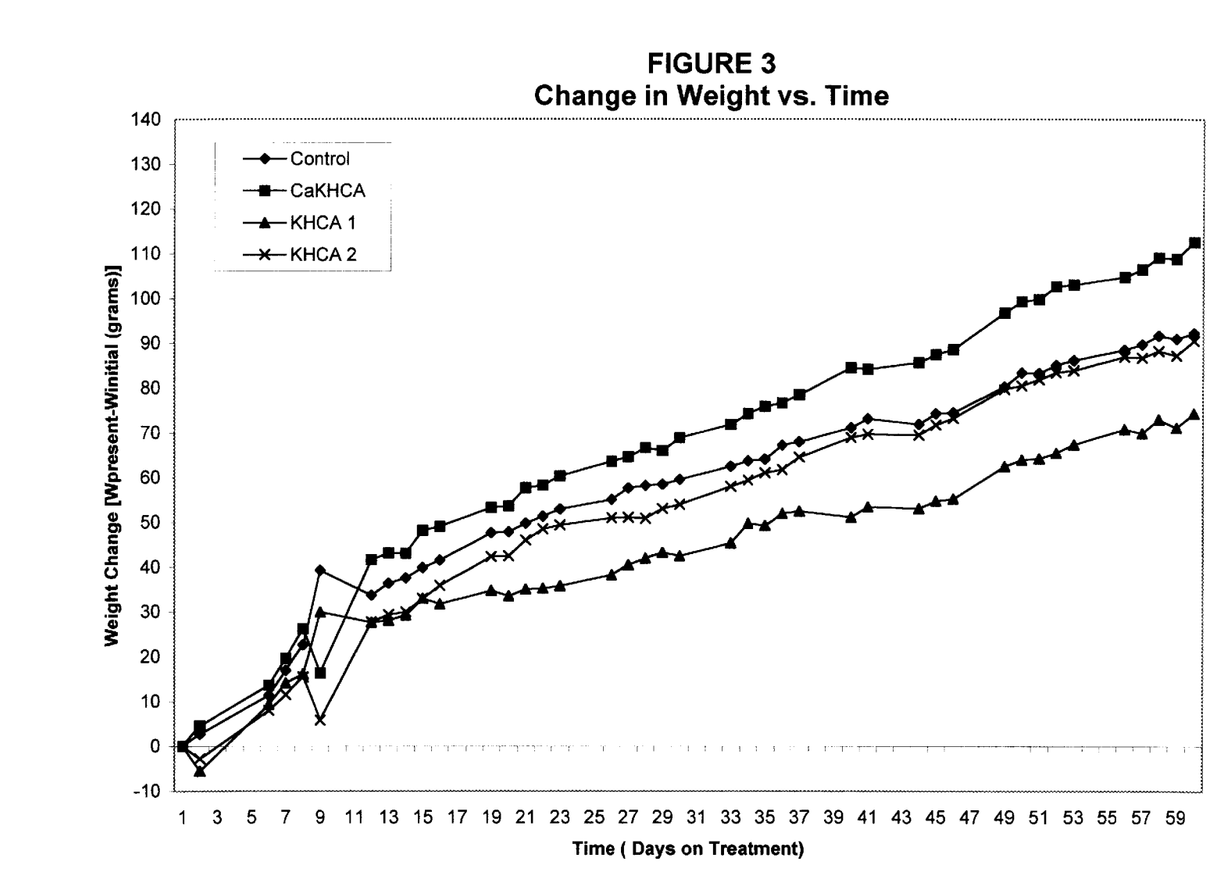
Figure 4:
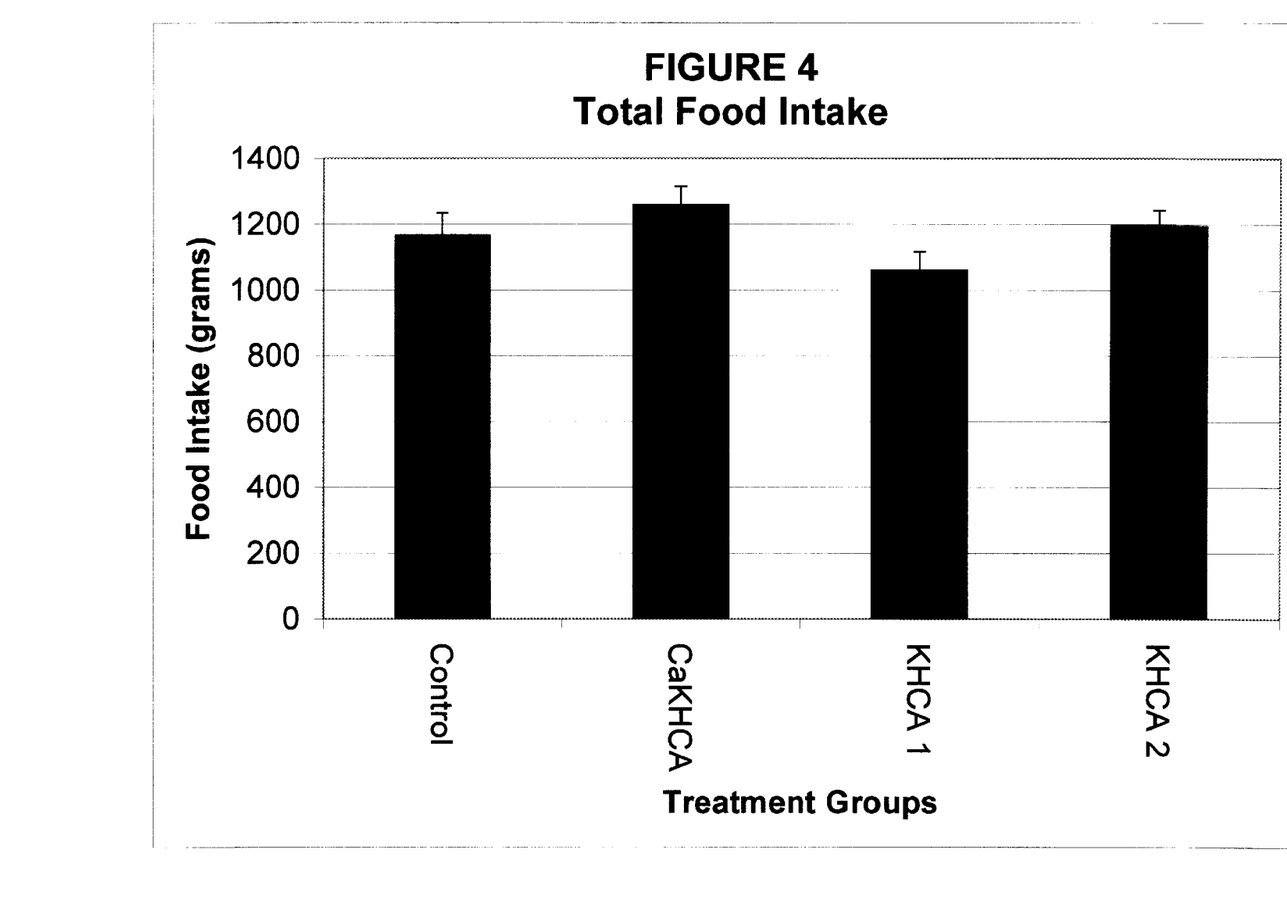

To test the properties of HCA in various forms under conditions similar to those found in human clinical trials, the authors arranged for male OM rats aged 10 weeks to be fed a diet in which 30% of the calories were obtained from fat under standard conditions. The rats were intubated twice daily with one of three HCA salts or placebo. The amount of HCA in each arm of 5 animals was the minimum dosage which had been found effective in the form of the pure trisodium salt of HCA in tests by Hoffman-La Roche in animals ingesting a 70% glucose diet, i.e., 0.33 mmoles/kg body weight HCA given twice per day. The HCA salts used were these: CaKHCA=a mixed calcium and potassium HCA salt commercially marketed as being entirely water soluble; KHCA 1 =a relatively clean, but still hardly pure potassium salt of HCA with a good mineral ligand attachment supplying 4467 mg potassium/100 grams of material; KHCA 2=an impure potassium salt of HCA with large amounts of gums attached and poor mineral ligand attachment supplying 2169 mg potassium/100 grams of material. FIGS. 1, 2 and 3 summarize our findings.

FIG. 1 shows the change in food intake over the 60 day period of the trial. Initial exposure to the highly palatable fatty diet after being raised on standard rat chow led to a period of elevated food intake in these rats which diminished for all arms over a period of roughly two weeks. Food intake at virtually all points was higher with the CaKHCA than in any other arm. Food intake was initially and remained largely the same in the control and KHCA 2 arms for the length of the trial. Food intake was markedly suppressed in the KHCA 1 arm for the first 25 days and remained quite noticeably depressed in comparison with the other arms for roughly seven weeks. During the last week of the study, however, food intake was only marginally less in the KHCA 1 arm than in the control and KECA 2 arms despite the lighter average weight of the animals in the KHCA 1 arm. The finding that the appetite suppression from the HCA diminished markedly by the end of the seventh week is in agreement with published data from Roche's animal trials, trials which used synthesized, hence pure HCA, typically in the form of the trisodium salt. The finding that the better quality KHCA 1 salt suppressed appetite and weight gain at this level of intake on a fatty diet rather than a 70% glucose diet indicates that the potassium salt is more active than is the sodium salt of HCA.

FIGS. 2 and 3 show the changes in average body weights in each arm over time and the average number of grams gained in weight in each arm over time. As can be seen from FIG. 2, the KHCA 1 group using the purer potassium salt began at an average weight almost the same as that of control, but diverged dramatically after about 9 days and remained strikingly lighter than control for the rest of the trial despite the convergence in food intakes at the end of the period. In contrast, the CaKHCA group increased its body weight vis-á-vis control from day 9 onward. The KHCA 2 group ingesting the poor quality potassium salt began as the heaviest of the arms (about 24 grams heavier than control) and ended the trial still about 24 grams, on average, heavier than control. FIG. 3 makes these points clearer. The lines showing the number of grams gained over time indicate quite directly that the CaKHCA salt group underwent significant weight gain in relation to control, the KHCA 2 group gained weight at a rate only slightly less than was true of control, and the KHCA 1 group obviously gained much less weight than did control. Below is the food intake data for the three active arms compared to that of control over the 60 days.

Total Food Intake

Total Food Intake (grams)

|  | Mean |
|---|---|
| Control | 1165.9 |
| CaKHCA | 1258.4 |
| KHCA 1 | 1060.1 |
| KHCA 2 | 1194.1 |
|  | Stdev |
| Control | 152.0 |
| CaKHCA | 126.7 |
| KHCA 1 | 127.5 |
| KHCA 2 | 109.0 |
|  | Avg FI |
| Control | 1238.98 |
| CaKHCA | 1320.44 |
| KHCA 1 | 1144.86 |
| KHCA 2 | 1275.30 |

This material supports the two biphasic attributes suggested here for HCA. In agreement with other researchers, the present authors have found that the appetite suppression of HCA does not appear to last for more than seven weeks in the rat model in normal animals. By day 60, any anorectic effect had disappeared in the study outlined here.

The biphasic dose response issue on a diet supplying a nontrivial percentage of its calories as fat apparently has not been explored before. In this study, the salts supplied to all three active arms contained the same amounts of HCA. Strikingly, the apparently lower availability of HCA for physiologic uptake or usage when delivered in the form of CaKHCA emerged despite the widespread assertion among commercial suppliers of HCA products that issues of bio-availability are adequately addressed simply by making the calcium salt of the compound soluble. Such is not the case. Similarly, the lower quality potassium salt, KHCA 2, in which inadequate amounts of potassium were available to fully occupy all bonding sites, proved to be no better, but also no worse, than placebo as a weight loss agent. Only the relatively clean and relatively fully reacted KHCA 1 showed any positive effect upon food consumption and weight gain in this model. The negative findings with the CaKHCA arm offer proof that the improper usage of HCA will increase the activity of acetyl CoA carboxylase, and, depending upon the dose and the diet, lead either to a null result or to a gain in appetite and weight. As can be seen in the following chart, at the level of intake used experimentally on a 30% fat diet, potassium HCA tends to increase protein as a percentage of body weight while reducing fat as a percentage of body weight. The CaKHCA salt, in contrast, increased fat and reduced protein as percentages of body weight. The relatively higher rates of body hydration found in the potassium salt-fed arms may represent elevated glycogen stores in muscle, an expected finding.

| Mean | Control | CaKHCA | KHCA 1 | KHCA 2 |
|---|---|---|---|---|
| % Body H₂O | 56.70 | 56.06 | 59.96 | 58.93 |
| % Protein | 18.66 | 17.77 | 18.95 | 20.07 |

-continued

| Mean | Control | CaKHCA | KHCA 1 | KHCA 2 |
|---|---|---|---|---|
| % Fat | 20.42 | 22.56 | 17.83 | 18.27 |
| % Ash | 2.98 | 2.37 | 3.04 | 2.61 |

EXAMPLE 3

Insulin, Leptin, Glucocorticoids & Resistin

Roche researchers in an animal experiment characterized by a 70% glucose diet found that despite the disappearance of appetite control, the trisodium salt of HCA maintained a reduced weight in animals as long at 80 days, at which point the experiment was terminated. (Sullivan A C, Triscari J. Metabolic regulation as a control for lipid disorders. I. Influence of (−)-hydroxycitrrate on experimentally induced obesity in the rodent. American Journal of Clinical Nutrition 1977;30:767.) The study by the present authors is the first to have shown that HCA positively influences the metabolism to prevent weight gain under normal dietary circumstances, that is, using middle aged animals and a diet which derives 30% of its calories from fat to mimic typical human age and diet as found in weight loss trials. This is a significant finding for several reasons. First, inasmuch as only quite small amounts of fats are synthesized from carbohydrates when fats supply even as little as 10% of the calories in the diet, the metabolic effect proposed by Roche and others as accounting for the efficacy of HCA in preventing weight gain, that is, the competitive inhibition of ATP:citrate lyase to influence signals sent from the liver, cannot have been a major factor in the study represented in FIGS. 1, 2, 3 and 4. Second, most scientific commentators on HCA up to the present point in time have accepted that animals will be insensitive to the appetite suppressive actions of the compound when on a cafeteria-style diet, which is the animal diet model appropriate for modeling human behavior and weight gain. (Bowden C R, White K D, Tutwiler G F. Energy intake of cafeteria-diet and chow-fed rats in response to amphetamine, fenfluramine, (−)-hydroxycitrate, and naloxone. The Journal of Obesity and Weight Regulation 1985 Spring;4(1):5–13.) The human weight loss trials cited previously would appear to confirm this position. However, again, the study represented in FIGS. 1, 2, 3 and 4 shows that HCA influences both appetite and metabolism even on a cafeteria-style diet when used properly.

The causal components of the long-term metabolic effects of HCA therefore would appear to be different in nature from those which induce the appetite suppression and most of the reduction in weight gain found with the compound for the first seven weeks of use. These same causal components when dysregulated, moreover, can be shown to be linked, as suggested above, as parts of a syndrome—the polymorphic metabolic syndrome—which, once active, tends to perpetuate itself To test these interrelations, data was collected from the rat study described above with regard to serum insulin, leptin and cortisol levels.

| Group | Insulin ng/mL | Leptin ng/mL | Corticosterone ng/mL |
|---|---|---|---|
| Control | 2.655 | 9.52 | 269.38 |
| Control | 7.077 | 18.94 | 497.87 |

-continued

| Group | Insulin ng/mL | Leptin ng/mL | Corticosterone ng/mL |
|---|---|---|---|
| Control | 4.280 | 34.34 | 265.71 |
| Control | 9.425 | 24.32 | 209.54 |
| Control | 3.798 | 8.40 | 116.12 |
| KHCA 1 | 3.880 | 9.93 | 45.79 |
| KHCA 1 | 4.399 | 7.31 | 33.10 |
| KHCA 1 | 3.181 | 9.25 | 65.57 |
| KHCA 1 | 3.210 | 24.36 | 55.40 |
| KHCA 1 | 3.639 | 9.07 | 84.62 |
| KHCA 2 | 4.427 | 9.13 | 26.02 |
| KHCA 2 | 4.301 | 9.75 | 270.83 |
| KHCA 2 | 3.245 | 8.00 | 45.44 |
| KHCA 2 | 3.695 | 9.16 | 45.63 |
| KHCA 2 | 2.053 | 8.26 | 38.04 |

Both of the potassium (−)-hydroxycitrate arms were superior to the calcium/potassium arm (data not shown here) in reducing insulin, leptin and corticosterone concentrations. Because of the difficulty in achieving significance with only 5 data points per arm, calculations regarding insulin and leptin combined the data from the two KHCA arms. With respect to insulin, the one-tailed P value was a significant 0.0306, and the two-tailed P value fell slightly short of significance at 0.0612. Using this combined data, there was also a significant one-tailed P value difference between the two KHCA arms and the result found with the CaKHCA. With respect to leptin, the two KHCA arms were combined, in part, because of one anomalously high data point and yielded a one-tailed P value which was a significant 0.0241 and a two-tailed P value which was significant at 0.0482. Corticosterone results were highly significant even at 5 data points per arm. KHCA 1 was easily significantly superior to control: the one-tailed P value was a highly significant 0.0048, and the two-tailed P value was a highly significant 0.0096.

Non-esterified fatty acid levels were not significantly different between control and the KHCA arms, but serum glucose and triglyceride levels exhibited a trend towards elevation. This is consistent with HCA's biophasic properties on a fatty diet and with published animal data to the effect that HCA elevates fatty acid oxidation at rest, although this effect is not significant during actual exercise. Elevated fatty acid oxidation typically slightly increases some fractions of blood fats, and also increases the rate of gluconeogenesis, hence may slightly increase blood glucose levels. However, in those individuals with markedly elevated blood glucose levels/glucose dysregulation, HCA can be used to improve glucose regulation. (U.S. Pat. No. 6,207,714) The same has been shown in animals with regard to elevated blood fats.

The clear implication of these data is that HCA, if supplied in appropriate amounts, may be useful in reducing insulin levels and insulin resistance, leptin levels and leptin resistance, and elevated glucocorticoid levels. The sustained reduction in weight gain found with KHCA 1 even after food consumption had returned to the level of control indicates an increased basal metabolic rate (BMR) and is in agreement with published studies already mentioned which give evidence of an increased BMR in HCA-treated animals.

It should be noted that an increased BMR is typical in cases in which fat consumption above the norm does not lead to weight gain. Elevated leptin blood levels have been found to correlate significantly in lean subjects with dietary fat intake and negatively with carbohydrate intake, whereas there is no correlation with total energy intake. Individuals who are lean on a chronically high fat diet (45% of calories) typically also have lower serum glucose levels. (Cooling J, Barth J, Blundell J. The high-fat phenotype: is leptin involved in the adaptive response to a high fat (high energy) diet? Int J Obes Relat Metab Disord. November 1998;22 (11): 1132–5.) This implies that some factor other than fatty acid oxidation, such as elevated insulin or glucocorticoid levels, has a role in inducing leptin resistance. Our findings suggest, based upon what is presently known of its actions, that the recently discovered signaling compound resistin likely is a common element involved in insulin resistance and leptin resistance which is affected by the chronic administration of adequate amounts of HCA. The impact of HCA upon resistin is itself mediated by way of peroxisome proliferator-activated receptor γ.

The evidence for this presently is indirect, yet a substantial case can be made. KHCA arms 1 and 2 significantly lowered insulin, leptin and glucocorticoid levels in comparison with control. This is important in that, as is true of insulin, in obese humans there is resistance to leptin and much elevated levels of leptin just as there is resistance to insulin and an elevated release of insulin. Elevated glucocorticoid levels increase leptin levels and may play a significant role in the development of leptin resistance, whereas norepinephrine and epinephrine decrease leptin production. (Fried S K, Ricci M R, Russell C D, Laferrere B. Regulation of leptin production in humans. J Nutr. December 2000; 130(12S Suppl):3127S-31 S.) Long ago, it was observed that HCA incubated with white fat cells had an effect similar to that observed with epinephrine. (Fried S K, Lavau M, Pi-Sunyer F X. Role of fatty acid synthesis in the control of insulin-stimulated glucose utilization by rat adipocytes. J Lipid Res. July 1981;22(5):753–62.)

Resistin levels are highly correlated with those of leptin. Resistin is exclusively made in adipose tissue. Moreover, its exclusive expression in adipocytes, its large increase during the late stage of adipogenesis, and its dramatic induction during fasting/refeeding and by insulin administration to streptozotocin-diabetic animals suggest that this factor may be involved in sensing the nutritional status of the animals to affect adipogenesis. Many of these properties are most similar to those observed with leptin, which is secreted only by adipocytes and is induced dramatically by fasting/refeeding and by diabetes/insulin. (Kee-Hong Kim, Kichoon Lee, Yang Soo Moon, and Hei Sook Sul. A Cysteine-rich Adipose Tissue-specific Secretory Factor Inhibits Adipocyte Differentiation. The Journal of Biological Chemistry Apr. 6, 2001;276(14): 11252–11256.) However, unlike resistin, leptin increases Krebs Cycle and uncoupling protein activity and it is an agonist for at least one peroxisome proliferator-activated receptor, that is, peroxisome proliferator-activated receptor a. (Ceddia R B, William W N Jr, Lima F B, Flandin P, Curi R, Giacobino J P. Leptin stimulates uncoupling protein-2 mRNA expression and Krebs cycle activity and inhibits lipid synthesis in isolated rat white adipocytes. Eur J Biochem. October;267(19):5952–8.)

The thiazolidinediones (TZDs), such as rosiglitazone, appear to work at least in part by down-regulating the expression of resistin while, and very likely by, up-regulating the actions of peroxisome proliferator-activated receptor γ (PPARγ). As with resistin, the biological functions of PPARγ seem to be connected to fuel sensing. Agonists for the latter increase energy expenditure and reduce insulin resistance. Significantly, the TZDs also down-regulate leptin gene expression, increase the flux through the Krebs Cycle and increase liver acetyl-CoA carboxylase, thus making cells more citrate-sensitive. As would be expected from this description, one side effect of rosiglitazone can be mild weight gain. (Thampy G K, Haas M J, Mooradian A D. Troglitazone stimulates acetyl-CoA carboxylase activity through a post-translational mechanism. Life Sci. Dec. 29, 2000;68(6):699–708.) Rosiglitazone is thought to have no liver toxicity, but troglitazone, another TZD, certainly does.

The similarities between the actions of HCA and the TZDs is remarkable. HCA reduces insulin and leptin levels, increases the flux through the Krebs Cycle, increases liver acetyl-CoA carboxylase and, in at least one sense, makes cells more citrate-sensitive. The latter actions likely are those which activate PPARγ, for it has been shown elsewhere that an increase in long-chain CoA (acyl-CoA) affects the PPARs. (Belfiore F, Jannello S. Insulin resistance in obesity: metabolic mechanisms and measurement methods. Mol Genet Metab. October 1998;65(2):121–8.) Activating PPARγ and reducing leptin levels, as already indicated, lowers resistin levels. (Steppan C M, Bailey S T, Bhat S, Brown E J, Banedee R R, Wright C M, Patel H R, Ahima R S, Lazar M A. The hormone resistin links obesity to diabetes. Nature. Jan. 18, 2001;409(6818):307–12.) Hence, in our view HCA provides the benefits and shares some of the primary mechanisms of action of the thiazolidinediones, but does not exhibit any of the toxicity found with some members of that class of drugs. When used properly, HCA not only does not promote the weight gain found with TZDs, it actually encourages weight loss.

Therefore, it is a novel and significant finding that HCA can be used to manipulate the resistin-PPARγ axis as well as the levels of insulin, leptin and glucocorticoids.

CONCLUSIONS (−)-Hydroxycitrate has a multitude of metabolic functions. The literature teaches that the compound reduces blood lipids, induces weight loss and decreases appetite in both animals and humans. However, the inventors have discovered that this compound corrects elements of the Polymorphic Metabolic Dysfunction (PMD). These include the dysregulation of the insulin, leptin and glucocorticoid pathways and the relationship of these to the resistin-peroxisome proliferator-activated receptor γ (PPARγ) axis. Therefore, (−)-hydroxycitrate may be useful in reducing insulin levels and insulin resistance, leptin levels and leptin resistance, and elevated glucocorticoid levels, which is to say that the compound appears to normalize the metabolism of insulin, leptin and the glucocorticoids. It further may be useful for normalizing the regulation of the resistin/peroxisome proliferator-activated receptor γ (PPARγ) axis. This safe and effective amelioration of the Polymorphic Metabolic Dysfunction is an entirely novel use of (−)-hydroxycitric acid, its derivatives and its salt forms.

We claim:

1. A method of treating or ameliorating Polymorphic Metabolic Dysfunction (PMD) in individuals in need thereof wherein PMD is characterized by glucocorticoid metabolism dysregulation, by administering an effective amount of (−)-hydroxycitric acid to influence the regulation of glucocorticoid metabolism and to influence the metabolism of leptin, resisten or peroxisome proliferator-activated receptor-γ(PPARγ).

2. A method for treating or ameliorating elevated glucocorticoid levels in individuals in need thereof which is comprised of administering orally an effective amount of (−)-hydroxycitric acid.

3. A method for treating or ameliorating elevated leptin levels and leptin resistance in individuals in need thereof which is comprised of administering orally an effective amount of (−)-hydroxycitric acid.

4. A method for treating or ameliorating elevated resistin levels in individuals in need thereof which is comprised of administering orally an effective amount of (−)-hydroxycitric acid.

5. A method for increasing peroxisome proliferator-activated receptor γ (PPARγ) activity in individuals in need thereof which is comprised of administering orally an effective amount of (−)-hydroxycitric acid.

6. The method of claim 1 where the (−)-hydroxycitric acid is supplied as a therapeutically effective amount of the free acid or its lactone.

7. The method of claim 1 where the (−)-hydroxycitric acid is supplied as a therapeutically effective amount of the alkali metal salts potassium or sodium (−)-hydroxycitrate.

8. The method of claim 1 where the (−)-hydroxycitric acid is supplied as a therapeutically effective amount of the alkaline earth metal salts calcium or magnesium (−)-hydroxycitrate.

9. The method of claim 1 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate or in the form of therapeutically effective amide and/or ester derivatives of (−)-hydroxycitric acid.

10. The method of claim 1 where the (−)-hydroxycitric acid is supplied as a therapeutically effective amount as the free acid, its lactone or as one or more of the salts or other derivatives of the free acid and is delivered in a controlled release form.

11. The method of claim 2 where the (−)-hydroxycitric acid is supplied as a therapeutically effective amount of the free acid or its lactone.

12. The method of claim 2 where the (−)-hydroxycitric acid is supplied as a therapeutically effective-amount of the alkali metal salts potassium or sodium (−)-hydroxycitrate.

13. The method of claim 2 where the (−)-hydroxycitric acid is supplied as a therapeutically effective amount of the alkaline earth metal salts calcium or magnesium (−)-hydroxycitrate.

14. The method of claim 2 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate or in the form of therapeutically effective amide and/or ester derivatives of (−)-hydroxycitric acid.

15. The method of claim 2 where the (−)-hydroxycitric acid is supplied as a therapeutically effective amount as the free acid, its lactone or as one or more of the salts or other derivatives of the free acid and is delivered in a controlled release form.

16. The method of claim 3 where the (−)-hydroxycitric acid is supplied as a therapeutically effective amount of the free acid or its lactone.

17. The method of claim 3 where the (−)-hydroxycitric acid is supplied as a therapeutically effective amount of the alkali metal salts potassium or sodium (−)-hydroxycitrate.

18. The method of claim 3 where the (−)-hydroxycitric acid is supplied as a therapeutically effective amount of the alkaline earth metal salts calcium or magnesium (−)-hydroxycitrate.

19. The method of claim 3 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate or in the form of therapeutically effective amide and/or ester derivatives of (−)-hydroxycitric acid.

20. The method of claim 3 where the (−)-hydroxycitric acid is supplied as a therapeutically effective amount as the free acid, its lactone or as one or more of the salts or other derivatives of the free acid and is delivered in a controlled release form.

21. The method of claim 4 where the (−)-hydroxycitric acid is supplied as a therapeutically effective amount of the free acid or its lactone.

22. The method of claim 4 where the (−)-hydroxycitric acid is supplied as a therapeutically effective amount of the alkali metal salts potassium or sodium (−)-hydroxycitrate.

23. The method of claim 4 where the (−)-hydroxycitric acid is supplied as a therapeutically effective amount of the alkaline earth metal salts calcium or magnesium (−)-hydroxycitrate.

24. The method of claim 4 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate or in the form of therapeutically effective amide and/or ester derivatives of (−)-hydroxycitric acid.

25. The method of claim 4 where the (−)-hydroxycitric acid is supplied as a therapeutically effective amount as the free acid, its lactone or as one or more of the salts or other derivatives of the free acid and is delivered in a controlled release form.

26. The method of claim 5 where the (−)-hydroxycitric acid is supplied as a therapeutically effective amount of the free acid or its lactone.

27. The method of claim 5 where the (−)-hydroxycitric acid is supplied as a therapeutically effective amount of the alkali metal salts potassium or sodium (−)-hydroxycitrate.

28. The method of claim 5 where the (−)-hydroxycitric acid is supplied as a therapeutically effective amount of the alkaline earth metal salts calcium or magnesium (−)-hydroxycitrate.

29. The method of claim 5 where the (−)-hydroxycitric acid is supplied as a therapeutically effective amount of a mixture the alkali metal salts and/or the alkaline earth metal salts of (−)-hydroxycitrate or some mixture of alkali metal salts and alkaline eart metal salts of (−)-hydroxycitrate or in the form of therapeutically effective amide and/or ester derivatives of (−)-hydroxycitric acid.

30. The method of claim 5 where the (−)-hydroxycitric acid is supplied as a therapeutically effective amount as the free acid, its lactone or as one or more of the salts or other derivatives of the free acid and is delivered in a controlled release form.

\* \* \* \* \*